(12) United States Patent
Detrembleur et al.

(10) Patent No.: US 6,686,424 B2
(45) Date of Patent: Feb. 3, 2004

(54) PREPARATION OF FUNCTIONALIZED ALKOXYAMINE INITIATOR AND ITS USE

(75) Inventors: Christophe Detrembleur, Köln (DE); Thomas Gross, Wülfrath (DE); Rolf-Volker Meyer, Much (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/464,927

(22) Filed: Jun. 19, 2003

(65) Prior Publication Data

US 2003/0236368 A1 Dec. 25, 2003

(30) Foreign Application Priority Data

Jun. 25, 2002 (EP) .............................. 02013949

(51) Int. Cl.[7] .......................... C08F 4/00; C07C 239/08
(52) U.S. Cl. ...................... 526/211; 526/204; 526/205; 526/220; 546/184; 548/542; 564/300; 564/301
(58) Field of Search ................ 564/300, 301; 546/184; 548/542; 526/204, 205, 211, 220

(56) References Cited

U.S. PATENT DOCUMENTS

| | | | |
|---|---|---|---|
| 4,581,429 A | 4/1986 | Solomon et al. ............ 526/220 |
| 5,322,912 A | 6/1994 | Georges et al. ............. 526/204 |
| 5,412,047 A | 5/1995 | Georges et al. ............. 526/204 |
| 5,449,724 A | 9/1995 | Moffat et al. ............... 526/204 |
| 5,498,679 A | 3/1996 | Moffat et al. ............... 526/204 |
| 6,255,422 B1 * | 7/2001 | Bertin et al. ................ 526/220 |
| 6,258,911 B1 | 7/2001 | Georges et al. ............. 526/346 |
| 6,353,107 B1 | 3/2002 | Kramer et al. .............. 546/216 |
| 6,495,720 B1 | 12/2002 | Couturier et al. ........... 564/301 |
| 6,569,967 B1 | 5/2003 | Couturier et al. ........... 526/193 |
| 2002/0007585 A1 * | 1/2002 | Pastor et al. ............ 564/300 X |
| 2002/0107397 A1 | 8/2002 | Kramer et al. .............. 546/192 |

FOREIGN PATENT DOCUMENTS

| CA | 2317321 | 3/2001 |
| CA | 2317323 | 3/2001 |
| EP | 0 891 986 | 1/1999 |

OTHER PUBLICATIONS

J. Am. Chem., Soc. 116, (month unavailable) 1994, pp. 11185–11186, Craig J. Hawker, Molecular Weight Control by a "Living" Free–Radical Polymerization Process.

J. Am. Chem. Soc., 121, (month unavailable) 1999, pp. 3904–3920, Didier Benoit, Vladimir Chaplinski, Rebecca Braslau and Craig J. Hawker, "Development of a Universal Alkoxyamine for "Living" Free Radical Polymerizations".

Macromolecules, 29, Jul. 29, 1996, pp. 5245–5254,Craig J. Hawker, Geroge G. Barclay, Arturo Orellana, Julian Dao and Wayne Devonport, "Initiating Systems for Nitroxide–Mediated "Living" Free Radical Polymerizations: Synthesis and Evaluation".

Macromolecules 31, (month unavailable) 1998, pp. 6727–6729, Dekun Wang and Zhe Wu, "Facile Synthesis of New Unimolecular Initiators for Living Radical Polymerizations".

Macromolecules 31, (month unavailable) 1998, pp. 4659–4661, Yozo Miura, Kenichi Hirota, Hiroaki Moto and Bunichiro Yamada, "High–Yield Synthesis of Alkoxyamine Initiators Carrying a Functional Group by Reaction of Ethylbenzenes with Di–tert–butyl Diperoxalate in the Presence of Nitroxides".

\* cited by examiner

*Primary Examiner*—Fred Teskin
(74) *Attorney, Agent, or Firm*—Joseph C. Gil; Aron Preis

(57) ABSTRACT

A one-pot process for the preparation of functional alkoxyamines of the general formula (I),

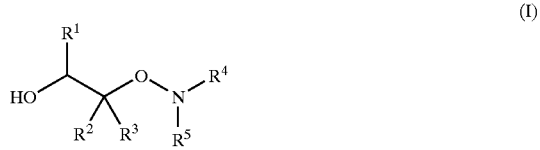

is disclosed. The process entails (1) reacting an oxidizing agent with a sterically hindered secondary amine to produce an aqueous phase and a nitroxyl radical (2) removing the aqueous phase and adding to the nitroxyl radical one or more vinyl monomer(s) conforming to a formula and a system which produces free radicals. Also disclosed is a process of polymerizing monomers using the functional alkoxyamine.

3 Claims, No Drawings

PREPARATION OF FUNCTIONALIZED ALKOXYAMINE INITIATOR AND ITS USE

FIELD OF THE INVENTION

The invention relates to a process for the preparation of functionalized alkoxyamine initiators and to their use in radical polymerization.

SUMMARY OF THE INVENTION

A one-pot process for the preparation of functional alkoxyamines of the general formula (I),

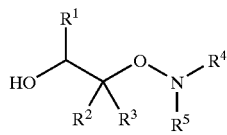

is disclosed. The process entails (1) reacting an oxidizing agent with a sterically hindered secondary amine to produce an aqueous phase and a nitroxy radical (2) removing the aqueous phase and adding to the nitroxy radical one or more vinyl monomer(s) conforming to a formula and a system which produces free radicals. Also disclosed is a process of polymerizing monomers using the functional alkoxyamine.

BACKGROUND OF THE INVENTION

The use of the controlled radical polymerization ("CRP") of vinyl monomers has increased rapidly because it allows the synthesis of a broad range of well-defined (co)polymers under uncomplicated experimental conditions. The polymerization may, for example, be carried out in aqueous media and under moderate polymerization temperatures and purification of the monomer prior to polymerization is not required. Additionally, the main molecular parameters of the polymer chain, for example its polydispersity, molecular weight, polymer architecture or the structure of the chain-ends may be easily controlled and adjusted. The CRP is also called "living" free radical polymerization. The aim of the precise control of free radical polymerization is achieved by reversible chain termination or blocking ("end-capping") after each growth step. The equilibrium concentration of the polymerization-active ("living") chain ends in this case is so low compared with the equilibrium concentration of the blocked ("dormant") chain ends that irreversible termination and transfer reactions are greatly suppressed compared with the growth reaction. Since the end-capping proceeds reversibly, all the chain ends remain "living" if no termination reagent is present. This allows the control of the molecular weight, low polydispersity and controlled functionalization of the chain ends by termination reagents.

Of all the CRP systems presently under investigation, the nitroxyl-mediated polymerization ("NMP") is one of the most attractive and efficient, because this technique provides advantages applicable to a broad range of monomers such as (meth)acrylates, acrylonitrile, styrenes, acrylamides, butadiene or isoprene and may be carried out in a metal-free, colorless and odorless manner.

Numerous publications have shown that alkoxyamines may be used to initiate and control the radical polymerization of vinyl monomers according to an NMP mechanism.

U.S. Pat. No. 4,581,429 discloses alkoxyamines which are formed by the reaction of linear or cyclic nitroxides, such as 2,2,6,6-tetra-methylpiperidin-1-oxyl (TEMPO) with organic carbon-based free radicals, and a process for the preparation of vinyl polymers using these compounds as initiators. The reactions typically have a low concentration of free radicals which, in the free radical polymerization of vinyl monomers, means that bimolecular termination reactions are less likely to occur than unimolecular growth reactions.

Other examples are described by Hawker et al. (*J. Am. Chem. Soc.* 1994, 116, 11185 and *J Am. Chem. Soc.* 1999, 121, 3904–3920) and in U.S. Pat. No. 5,322,912, U.S. Pat. No. 5,412,047, U.S. Pat. No. 5,449,724, U.S. Pat. No. 5,498,679, U.S. Pat. No. 6,258,911, DE-A 199 09 767 and EP-A 0 891 986.

The most commonly used method for the synthesis of alkoxyamines consists in coupling an alkyl radical to a nitroxyl radical. The alkyl radical $R^0$ may be generated by different methods, for example by decomposition of azo compounds (Hawker et al., Macromolecules 1996, 29, 5245–5254; Yozu Miura et al., Macromolecules 1998, 31, 6727–6729), by hydrogen removal from an appropriate substrate (Hawker et al., Macromolecules 1996, 29, 5245–5254; Yozu Miura et al., Macromolecules 1998, 31, 4659–4661) or by addition of a radical to an olefin (Hawker et al., J. Am. Chem. Soc. 1994, 116, 11185). The alkyl radical may also be generated from an halogenated compound R—X in the presence of a metallic catalyst following an atom transfer radical addition ("ATRA") reaction (WO-A 00/49027; WO-A 00/61544).

EP-A 1 083 169 discloses a process for the preparation of functionalized alkoxy-amine initiators in which hydrogen peroxide is reacted with iron(II) sulfate in the presence of a nitroxyl radical and a vinyl monomer to form the alkoxyamine with a good yield in a one-pot process.

The major disadvantage of the methods described above is that the alkoxyamines have to be synthesised from costly nitroxyl radicals and generally must be purified before they may be used for polymerization.

The object of the present invention was to provide a new synthetic pathway for the synthesis of alkoxyamines in a one-pot process and to use these alkoxyamines as intermediates in a polymerization process which provides homo- and copolymers of narrow polydispersity with a specific molecular weight and which does not have the above-mentioned disadvantages of the prior art.

DETAILED DESCRIPTION OF THE INVENTION

Surprisingly, it has now been found that hydroxy-functional alkoxyamines may be produced from secondary amines in a one-pot process and used, without intermediate purification, in a controlled, free-radical polymerisation process.

The object of the present invention is a one-pot process for the preparation of functional alkoxyamines of the general formula (I)

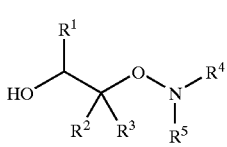

wherein $R^1$, $R^2$, $R^3$ are independently selected from the group consisting of: hydrogen, $C_1$–$C_{20}$ alkyl, $C_1$–$C_{20}$cycloalkyl, $C_6$–$C_{24}$aryl, halogen, cyano, $C_1$–$C_{20}$alkylester $C_1$–$C_{20}$cycloalkylester, $C_1$–$C_{20}$alkylamide, $C_1$–$C_{20}$cycloalkylamide $C_6$–$C_{24}$-arylester and $C_6$–$C_{24}$-arylamide;

$R^4$ and $R^5$ are independently selected from the group consisting of: $C_1$–$C_{18}$alkyl, $C_2$–$C_{18}$alkenyl, $C_2$–$C_{18}$alkynyl, $C_3$–$C_{12}$cycloalkyl, $C_3$–$C_{12}$heterocycloalkyl, and $C_6$–$C_{24}$-aryl, all of which are optionally substituted by $NO_2$, halogen, amino, hydroxy, cyano, carboxy, ketone, $C_1$–$C_4$alkoxy, $C_1$–$C_4$alkylthio, $C_1$–$C_4$alkylamino; or $R^4$ and $R^5$ form, together with the nitrogen atom linking them, a $C_3$–$C_{12}$cycloalkyl radical, a ($C_4$–$C_{12}$alkanol)yl radical or a $C_2$–$C_{13}$-heterocycloalkyl radical containing oxygen, sulfur or nitrogen atoms; or $R^4$ and $R^5$ together form a residue of a polycyclic ring system or a polycyclic heterocycloaliphatic ring system containing oxygen, sulfur or nitrogen atoms;

wherein the carbon atom of the $R^4$ and $R^5$ radicals directly adjacent to the alkoxyamine nitrogen atom is in each case substituted by 3 further organic substituents and wherein optionally at least one of the radicals $R^4$ and $R^5$ contains a functional group Y which is capable of further reacting or crosslinking with the functional groups known from the coatings field;

comprising the reaction steps of (1) reacting of an oxidizing agent (A) with a sterically hindered secondary amine of the general formula (II),

(II)

wherein $R^4$ and $R^5$ are independently selected from the group consisting of: $C_1$–$C_{18}$alkyl, $C_2$–$C_{18}$-alkenyl, $C_2$–$C_{18}$alkynyl, $C_3$–$C_{12}$cyclo-alkyl or $C_3$–$C_{12}$-heterocycloalkyl, $C_6$–$C_{24}$aryl, all of which are optionally substituted by $NO_2$, halogen, amino, hydroxy, cyano, carboxy, ketone, $C_1$–$C_4$alkoxy, $C_1$–$C_4$alkylthio, $C_1$–$C_4$alkylamino; or $R^4$ and $R^5$ form, together with the nitrogen atom linking them, a $C_3$–$C_{12}$cycloalkyl radical, a ($C_4$–$C_{12}$alkanol)yl radical or a $C_2$–$C_{13}$heterocycloalkyl radical containing oxygen, sulfur or nitrogen atoms; or $R^4$ and $R^5$ together form a residue of a polycyclic ring system or a polycyclic heterocycloaliphatic ring system containing oxygen, sulfur or nitrogen atoms;

wherein the carbon atom of the $R^4$ and $R^5$ radicals directly adjacent to the alkoxyamine nitrogen atom is in each case substituted by 3 further organic substituents and wherein optionally at least one of the radicals $R^4$ and $R^5$ contains a functional group Y which is capable of further reacting or crosslinking with functional groups known in the coatings field;

in a water-containing medium, to form an aqueous phase and nitroxyl radicals, (2) removing of the aqueous phase and (3) adding to the nitroxyl radicals one or more monomer(s) of the general formula (III),

wherein $R^1, R^2, R^3$ are independently selected from the group consisting of: hydrogen, $C_1$–$C_{20}$alkyl, $C_1$–$C_{20}$cycloalkyl $C_6$–$C_{24}$aryl, halogen, cyano, $C_1$–$C_{20}$alkylester $C_1$–$C_{20}$cycloalkylester, $C_1$–$C_{20}$alkylamide, $C_1$–$C_{20}$cycloalkylamide $C_6$–$C_{24}$-arylester and $C_6$–$C_{24}$-arylamide;

as well as (B) a system which produces free radicals that contains (B1) a reducing agent and (B2) a molecule able to react with (B1) to form radicals.

The Y group is capable of reacting further or crosslinking and is for example hydroxyl, carboxy, amino, isocyanate, urethane or epoxide groups.

Suitable oxidizing agents (A) are all oxidizing agents known from the prior art for the oxidation of secondary amines into nitroxyl radicals (Rozantsev et al. Synthesis 1971, 4, 192–195). Preferred oxidizing agents are water-soluble oxidizing agents, such as peracids such as peracetic acid, perpropionic acid, m-chloroperbenzoic acid, dimethyldioxirane, perbenzoic acid, or peroxides such as potassium peroxymonosulfate (Oxone®, DuPont Specialty Chemistry, USA), hydrogen peroxide, hydrogen peroxide/sodium tungstate, hydrogen peroxides/titanium containing catalysts, such as for example titanium dioxide and titanium silicalites (EP-A 0 488 403, page 5), phosphotungstic acid and oxidizing gases such as molecular oxygen or ozone. Particularly preferred are peracetic acid, perpropionic acid, m-chloro-perbenzoic acid, Oxone® (DuPont Specialty Chemistry, USA) and hydrogen peroxide/sodium tungstate.

Metal oxides such as silver oxide, lead (IV) oxide and sodium tungstate may also be used, optionally in combination with another oxidizing agent. A mixture of various oxidizing agents may also be used.

The water-containing medium in which the secondary amine is dispersed may contain a basic organic or inorganic buffer or organic or inorganic bases, such as $Na_2CO_3$, $NaHCO_3$, $K_2CO_3$, $KHCO_3$, $Na_3PO_4$, $Na_2HPO_4$, $NaH_2PO_4$, metal salts of carboxylic acids such as acetic acid sodium salt or propionic acid sodium salt, or a mixture thereof. $Na_2CO_3$, $NaHCO_3$, $K_2CO_3$, $KHCO_3$ and the sodium, calcium or potassium salts of acetic acid are preferred.

Useful sterically hindered secondary amines of the general formula (II) are for example those of the following formulare (IV) to (XII):

(IV)

-continued

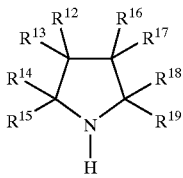
(V)

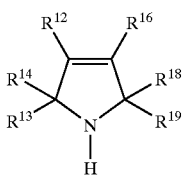
(VI)

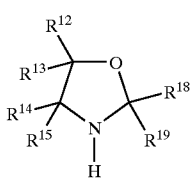
(VII)

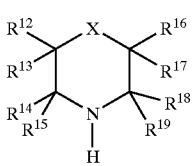
(VIII)

wherein
$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R_{19}$ are independently selected from a first group consisting of: hydrogen, halogen or cyano-, amide-, ether-, ester-, thioether-, ketone-, amide-, carbomyl-, amidine- or dialkylphosphonyl-containing groups; or a second group consisting of: $C_1$–$C_{18}$alkyl, $C_2$–$C_{18}$alkenyl, $C_2$–$C_{18}$alkynyl, $C_3$–$C_{12}$cycloalkyl or $C_3$–$C_{12}$heterocycloalkyl, $C_6$–$C_{24}$aryl, all of which are optionally substituted by $NO_2$, halogen, amino, hydroxy, cyano, carboxy, $C_1$–$C_4$alkoxy, $C_1$–$C_4$alkylthio, $C_1$–$C_4$alkylamino; or $R^6$ to $R^{19}$ may form, together with the carbon atom linking them, a $C_3$–$C_{12}$-cycloalkyl radical, a ($C_4$–$C_{12}$alkanol)yl radical or a $C_2$–$C_{13}$heterocycloalkyl radical containing oxygen, sulfur or nitrogen atoms;

$R^6$ to $R^{19}$ together form a residue of a polycyclic ring system or a polycyclic heterocycloaliphatic ring system containing oxygen, sulfur or nitrogen atoms;
wherein optionally at least one of the radicals $R^6$ to $R^{19}$ contains a functional group Y which is capable of reacting further or of cross-linking with functional groups known in the coatings field and X represents a methylene, ketone, ester group or oxygen atom, a hydrocarbon radical, which may be substituted by a cyano, nitro, ether, ester, hydroxy or imido group.

Other useful secondary amines are for example those of the following formulae (IX) and (X):

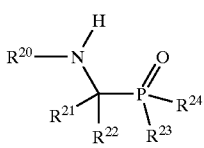
(IX)

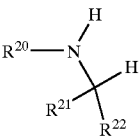
(X)

wherein
$R^{20}$ is selected from the group consisting of $C_1$–$C_{18}$alkyl, $C_2$–$C_{18}$alkenyl, $C_2$–$C_{18}$alkynyl, $C_3$–$C_{12}$cycloalkyl, $C_3$–$C_{12}$heterocycloalkyl and $C_6$–$C_{24}$aryl, all of which are optionally substituted by $NO_2$, halogen, amino, hydroxy, cyano, carboxy, $C_1$–$C_4$alkoxy, $C_1$–$C_4$alkylthio, $C_1$–$C_4$alkylamino;

$R^{20}$ may optionally contain a functional group Y which is capable of reacting further or of crosslinking with the functional groups known from the coatings field;

$R^{21}$, $R^{22}$ are independently selected from a first group consisting of: hydrogen, halogen or cyano-, amide-, ether-, ester-, thioether-, ketone-, amide-, carbomyl-, amidine- and dialkylphosphonyl-containing groups; and a second group consisting of: $C_1$–$C_{18}$alkyl, $C_2$–$C_{18}$alkenyl, $C_2$–$C_{18}$alkynyl, $C_3$–$C_{12}$cycloalkyl, $C_3$–$C_{12}$heterocycloalkyl, and $C_6$–$C_{24}$aryl, which are optionally substituted by $NO_2$, halogen, amino, hydroxy, cyano, carboxy, $C_1$–$C_4$alkoxy, $C_1$–$C_4$alkylthio or $C_1$–$C_4$alkylamino;

$R^{21}$ and $R^{22}$ optionally form, together with the carbon atom linking them, a $C_3$–$C_{12}$cycloalkyl radical, a ($C_4$–$C_{12}$alkanol)yl radical or a $C_2$–$C_{13}$heterocycloalkyl radical containing oxygen, sulfur or nitrogen atoms; or may together form a residue of a polycyclic ring system or a polycyclic heterocycloaliphatic ring system containing oxygen, sulfur or nitrogen atoms;

wherein $R^{23}$ and $R^{24}$ optionally form, together with the phosphorus atom linking them, a $C_3$–$C_{12}$cycloalkyl radical, a ($C_4$–$C_{12}$alkanol)yl radical or a $C_2$–$C_{13}$heterocycloalkyl radical containing oxygen, sulfur or nitrogen atoms;

wherein optionally at least one of the radicals $R^{20}$ to $R^{24}$ contains a functional group Y which is capable of further reacting or of crosslinking with functional groups known from the coatings field;

$R^{23}$, $R^{24}$ are independently selected from the group consisting of: $C_1$–$C_{18}$alkyl, $C_2$–$C_{18}$alkenyl, $C_2$–$C_{18}$alkynyl, $C_3$–$C_{12}$cycloalkyl, $C_3$–$C_{12}$heterocycloalkyl and $C_6$–$C_{24}$aryl, all of which are optionally substituted by $NO_2$, halogen, amino, hydroxy, cyano, carboxy, $C_1$–$C_4$alkoxy, $C_1$–$C_4$alkylthio or $C_1$–$C_4$ alkyl amino; or $R^{23}$ and $R^{24}$ optionally form, together with the phosphorus atom linking them, a $C_3$–$C_{12}$cycloalkyl radical, a ($C_4$–$C_{12}$alkanol)yl radical or a $C_2$–$C_{13}$heterocycloalkyl radical containing oxygen, sulfur or nitrogen atoms;

wherein at least one of the radicals $R^{23}$ to $R^{24}$ optionally contains a functional group Y which is capable of further reacting or of crosslinking with functional groups is known from the coatings field.

Preferred secondary amines of the general formula (II) are tert-butyl amine; 2,2,6,6-tetramethylpiperidine; 4-hydroxy-2,2,6,6-tetramethylpiperidine; 2,2,6,6-tetramethyl-4-piperidinone; 2,2,6,6-tetramethyl-4-piperidinyl acetate; 2,2, 6,6-tetramethyl-4-piperidinyl stearate; 2,2,6,6-tetramethyl-4-piperidinyl benzoate; 2,6-dimethyl-2,6-diethylpiperidine; diethyl 1-(tert-butylamino)-2,2-dimethylpropylphosphonate; dipropyl 1-(tert-butylamino)-2,2-dimethylpropylphosphonate; dibutyl 1-(tert-butylamino)-2,2-dimethylpropylphosphonate; N-(tert-butyl)-1-(diethylphosphoryl)-2,2-dimethyl-1-propylamine; N-(tert-butyl)-1-(dipropyl-phosphoryl)-2,2-dimethyl-1-propylamine; N-(tert-butyl)-2-methyl-1-phenyl-1-propylamine; 2,2,4,6,6-pentamethyl-1,2,5,6-tetrahydropyrimidine; N-[(3E)-2,2-diphenyl-1,2-dihydro-3H-indol-3-ylidene]-N-phenylamine; 2,6-diethyl-2,3,6-trimethyl-4-piperidinone; 2,6-diethyl-2,3,6-trimethyl-4-piperidinol; 14-oxa-7-azadispiro[5.1.5.2]pentadecane; 2,2,4,4-tetramethyl-1,3-oxazolidine; 2,2,5,5-tetramethyl-1-pyrrolidine; 3-carboxy-2,2,5,5-tetramethyl-1-pyrrolidine; 2,5-diphenyl-2,5-dimethylpyrrolidine; 3-carboxy-2,5-diphenyl-2,5-dimethyl-pyrrolidine; 1,1,3,3-tetraethylisoindoline; 1,1,3,3-tetramethylisoindoline; 1,1,3,3-tetrapro-pylisoindoline.

Particularly preferred are: tert-butyl amine; 2,2,6,6-tetramethylpiperidine; 4-hydroxy-2,2,6,6-tetramethylpiperidine; 2,2,6,6-tetramethyl-4-piperidinone; 2,2,6,6-tetramethyl-4-piperidinyl acetate; diethyl 1-(tert-butylamino)-2,2-dimethylpropyl phosphonate; dipropyl 1-(tert-butylamino)-2,2-dimethylpropyl phosphonate; dibutyl 1-(tert-butylamino)-2,2-dimethylpropyl phosphonate; 2,6-diethyl-2,3,6-trimethyl-4-piperidinone; 2,6-diethyl-2,3,6-trimethyl-4-piperidinol; 2,2,5,5-tetramethyl-1-pyrrolidine; 1,1,3,3-tetramethylisoindoline.

Polyfunctional amines may also be used as compounds of the formula (II) in order to form resins displaying heat reversibility. In the context of the present invention polyfunctional amines are compounds which have more than one secondary amino group. These properties are particularly interesting when low viscosity of the polymer is required during processing.

Some examples of suitable polyfunctional amines are bis(2,2,6,6-tetramethylpiperidine) sebacate; bis(2,2,6,6-tetramethylpiperidine) succinate; bis(2,2,6,6-tetramethylpiperidine) adipate; bis(2,2,6,6-tetramethylpiperidine) phthalate; bis(2,2,6,6-tetramethylpiperidine) isophthalate; bis(2,2,6,6-tetramethylpiperidine) terephthalate; or polymeric multifunctional amines such as poly((6-((1,1,3,3-tetramethylbutyl)amino)-1,3,5-triazine-2,4-diyl)((2,2,6,6-tetramethyl-4-piperidinyl)imino)-1,6-hexanediyl((2,2,6,6-tetramethyl-4-piperidinyl)imino)) (CHIMASSORB® 944, Ciba Specialty Chemicals, D-Lampertheim).

Typical monoethylenically unsaturated monomers which are suitable for the present invention are the alkyl esters of acrylic or methacrylic acids, such as methyl acrylate, ethyl acrylate, butyl acrylate, methyl methacrylate, ethyl methacrylate, butyl methacrylate and isobutyl methacrylate; the hydroxyalkyl esters of acrylic or methacrylic acids, such as hydroxyethyl acrylate, hydroxypropyl acrylate, hydroxyethyl methacrylate and hydroxypropyl methacrylate; acrylamide, methacrylamide, N-tertiary butylacrylamide, N-methylacrylamide, N,N-dimethylacrylamide; acrylonitrile, methacrylonitrile, allyl alcohol, dimethylaminoethyl acrylate, dimethylaminoethyl methacrylate, phosphoethyl methacrylate, N-vinylpyrrolidone, N-vinylformamide, N-vinylimidazole, vinyl acetate, conjugated dienes such as butadiene or isoprene, styrene, styrenesulfonic acid salts, vinylsulfonic acid salts and 2-acrylamido-2-methylpropane-sulfonic acid salts and acryloyl. Also suitable are cis- and trans-stilbene and diphenylethylene.

Examples of comonomers suitable for use in the present invention are $C_3$–$C_6$-ethylenically unsaturated monocarboxylic acids as well as the alkali metal salts and ammonium salts thereof. The $C_3$–$C_6$-ethylenically unsaturated monocarboxylic acids include acrylic acid, methacrylic acid, crotonic acid, vinylacetic acid and acryloxypropionic acid. Acrylic acid and methacrylic acid are the preferred monoethylenically unsaturated monocarboxylic acid monomers.

Examples of $C_8$–$C_{16}$-ethylenically unsaturated phenolic compounds which may also be used as comonomers are 4-hydroxy styrene, 4-hydroxy, α-methyl styrene, 2,6-ditert-butyl and 4-vinyl phenol.

Another class of carboxylic acid monomers suitable for use as comonomers in this invention are $C_4$–$C_6$-ethylenically unsaturated dicarboxylic acids and the alkali metal and ammonium salts thereof as well as the anhydrides of cis-dicarboxylic acids. Suitable examples include maleic acid, maleic anhydride, itaconic acid, mesaconic acid, fumaric acid and citraconic acid. Maleic anhydride (and itaconic acid) is the preferred monoethylenically unsaturated dicarboxylic acid monomer(s).

The acid monomers suitable for use in the present invention may be in the form of their acids or in the form of the alkali metal salts or ammonium salts of the acid.

Preferred monomers are selected from the group consisting of (meth)acrylic acid esters of $C_1$–$C_{20}$-alcohols, acrylonitrile, cyanoacrylic acid esters of $C_1$–$C_{20}$-alcohols, maleic acid diesters of $C_1$–$C_6$-alcohols, maleic anhydride, vinyl-pyridines, vinyl(alkylpyrroles), vinyloxazoles, vinyloxazolines, vinylthiazoles, vinylimidazoles, vinylpyrimidines, vinyl ketones, styrene or styrene derivatives which contain a $C_1$–$C_6$-alkyl radical or halogen in the α-position and contain up to 3 additional substituents on the aromatic ring. Nonpolymerizable vinyl monomers such as cis- and trans-stilbene, and diphenylethylene are also preferred.

Particularly preferred monomers are methyl acrylate, methyl methacrylate, butyl acrylate, butyl methacrylate, 2-ethylhexyl acrylate, cyclohexyl methacrylate, iso-bornyl methacrylate, maleic anhydride, styrene or acrylonitrile.

The compound (B1) is a reducing agent, such as for example transition metal compounds, sulfur compounds of a low degree oxidation or compounds which may be readily enolized. Preferred are sodium hydrogen sulfite, reducing sugars such as a glucose and dextrose, carbonyl compounds which may be readily enolized, such as ascorbic acid and hydroxyacetone, and metal ions, such as $Fe^{2+}$, $Ti^{3+}$ and $Cu^{1+}$. Particularly preferred are $Fe^{2+}$, $Ti^{3+}$ and $Cu^{1+}$ in the form of inorganic salts or organic salts.

Component (B2) is a molecule able to react with (B1) to form one or more free radicals. Hydrogen peroxide is preferably employed as component (B2) in the context of the present invention.

Hydrogen peroxide is a thermodynamically metastable compound in the form of the pure substance and in aqueous solution (e.g. 30% perhydrol). The rate of dissociation of hydrogen peroxide is greatly increased, even at room temperature, by catalysts, (e.g. finely divided metals, manganese dioxide, dust particles, non-metal ions, such as $I^-$, $IO_3^-$ and $OH^{31}$, or metal ions, such as $Fe^{2+}$, $Fe^{3+}$ and $Cu^{2+}$). Hydroxyl radicals may be generated in a controlled manner from hydrogen peroxide by thermal decomposition of the hydrogen peroxide or by one-electron redox reactions of the hydrogen peroxide with a suitable electron donor. Typical compounds are for example sodium hydrogen sulfite, carbonyl compounds which may be readily enolized, such as ascorbic acid and hydroxyacetone, and metal ions, such as $Fe^{2+}$, $Ti^{3+}$ and $Cu^{1+}$. The reaction of $Fe^{2+}$ with hydrogen peroxide to give hydroxyl radicals which may be used for oxidation of organic compounds has become known by the name of Fenton's reagent. The hydroxyl anion formed in the redox reaction may also initiate the peroxide dissociation.

In the process according to the invention for the preparation of an alkoxyarnine initiator of the formula (I), an hydroxyl radical (generated from $H_2O_2$ and reducing agent B1) adds on to a C=C double bond of the monomer of the general formula (III) thus introducing the hydroxyl group into the monomer of the general formula (III) which is then reacted with the nitroxyl radical to form the alkoxyamine initiator (I).

In principle, other compounds of the type R'—O—O—R" may also be used as component (B2). The radicals R' and R" may contain a functional group Y which is capable of further reacting or of crosslinking with the functional groups known from the coatings field, for example OH, $NH_2$, NHR or epoxide.

One way of carrying out the invention is that in the first step the secondary amine of formula (II) is introduced into a reaction vessel containing water-containing medium. The weight ratio of water to secondary amine is in the range of about 0.1 to 200, preferably about 1 to 50, and more preferably about 2 to 30. It is preferred that the water contains a basic inorganic or organic buffer or inorganic or organic bases. The molar ratio of secondary amine to buffer or base is in the range from about 20 to 0.05, preferably about 10 to 0.1, more preferably about 5 to 0.5.

Preferably the secondary amine of formula (II) is dissolved in a suitable solvent that is immiscible in water, in order to form a biphasic medium. Preferred solvents are toluene, xylene or dichloromethane. The solvent to secondary amine weight ratio is in the range from about 0.1 to 30, preferably about 0.5 to 10, and more preferably about 1 to 5.

While stirring vigorously, the oxidizing agent (A) is then slowly added in its pure form to the reaction vessel containing the secondary amine of formula (II). It is also possible to add a solution of the oxidizing agent (A) to the reaction vessel. Suitable solvents used for that purpose are inert towards the various reagents and do not react during the reaction: they are for example toluene, xylene, dichloromethane. When the oxidizing agent (A) is water-soluble, the preferred solvent is water. The solvent to oxidizing agent weight ratio is in the range from about 0.1 to 30, preferably about 0.5 to 10, and more preferably about 1 to 5.

With certain functional groups (e.g. Y=$NH_2$), it may be advantageous to provide the functional groups with a protective group during the reaction described (e.g. protection of amino groups as acetamides; Later liberation of the amido function by hydrolysis with a base); for Y=OH, however, it is not necessary to use protective groups.

The temperature of the reaction may range from about $-10°$ C. to about $100°$ C., preferably about $0°$ C. to $80°$ C., and more preferably about $0°$ C. to $40°$ C. The reaction time may range from about 10 minutes to about 72 h, preferably about 1 h to 36 h, and more preferably about 2 h to 24 h. The first step of the process of the present invention may be carried out in air or in an inert gas atmosphere such as nitrogen or argon.

In the second step, after the partial or complete oxidation of the secondary amine to form a nitroxyl radical, stirring is terminated and the aqueous phase is removed.

In the third step, the vinyl monomer of formula (III), component (B1) and optionally some additional solvents are added to the organic phase of step two. Suitable solvents for the third step of the process are water, alcohols, preferably methanol, ethanol or isopropanol, ethers, preferably diethylether, oligoethylene glycols or THF, carbonyl compounds, preferably acetaldehyde, acetone or methyl ethyl ketone, or any desired mixtures of the solvents mentioned. While stirring component (B2) is slowly metered in. It is therefore possible to add component (B2) in the form of an aqueous solution.

Component (B2) is used a 0.1- to 20-fold molar excess based on the initial secondary amine. Component (B1) is used in an equimolar amount, but preferably in an up to 20% molar excess, based on the secondary amine initially introduced. The vinyl monomer of formula (III) is used in a 0.2- to 20-fold molar excess, based on the secondary amine initially introduced. The reaction temperature may range from about $-10°$ C. to $150°$ C., preferably $0°$ C. to $100°$ C., and more preferably $25°$ C. to $60°$ C. The reaction may be carried out in air or in an inert gas atmosphere, preferably in an inert gas atmosphere such as in nitrogen or argon. The pH of the reaction solution may optionally be adjusted to a range from 5 to 7 with substances such as $NaHCO_3$.

After the reaction is complete, the solution may be optionally filtered in order to remove any solid residue such as iron(III) salts. The residual monomer of formula (III), solvents and oxidizing agent (A), if volatile, are removed in vacuo. An organic solvent not miscible with water is added and the organic phase is washed with acidic water (pH≈5–2) in order to remove the residual secondary amine. Optionally, the organic phase may be washed with basic water (pH≈7.5–9.5) and/or reducing agents, in order to remove excess oxidizing agent. The organic phase is then dried under a drying agent such as $Na_2SO_4$ or $MgSO_4$. The elimination of the solvent under vacuum provides the crude alkoxyamines of the formula (I).

Another object of the present invention is to provide a new process for preparing oligomers, cooligomers, polymers or block or random copolymers, which comprises preparing the functional alkoxyamines of formula (I) according to the process of the present invention and adding at least one polymerizable monomer to the unpurified alkoxyamine of formula (I) followed by heating.

An important advantage of the process according to the present invention is that an additional purification step of the alkoxyamines may be dispensed with.

For the preparation of the (co)polymers according to the present invention, all the components such as monomer(s), crude alkoxyamine of the formula (I) are reacted at a temperature ranging from about $0°$ C. to $260°$ C., preferably about $50°$ C. to $200°$ C., and more preferably about $70°$ C. to $150°$ C., for a period of time ranging from about 30 minutes to 72 hours, preferably about 1 hour to 48 hours, more preferably about 2 hours to 24 hours. The polymerization is carried out in an inert gas atmosphere, for example nitrogen or argon.

Optionally, some additives may be added to the polymerization medium before the polymerization or during the polymerization process in order to accelerate the polymerization. Such additives are well-known in the art and are for example camphorsulfonic acid, 2-fluoro-1-methylpyridinium p-toluenesulfonate, acylating compounds such as acetic anhydride (Tetrahedron 1997, 53(45), 15225), glucose, dextrose (Macromolecules 1998, 31, 7559), ascorbic acid (Macromolecules 2001, 34, 6531) or long-life radical initiators as reported in U.S. Pat. No. 6,288,186 (column 4, lines 8–24).

Suitable monomers are the water-soluble and water-insoluble polymerizable monomers mentioned above.

The (co)polymers of the present invention may have a number average molecular weight of from 1000 to $2 \cdot 10^6$, preferably from 2000 to $5 \cdot 10^5$, more preferably from 2000 to $2.5 \cdot 10^5$.

The alkoxyamine compound of the formula (I) is introduced in a quantity ranging from about 20 wt % to 0.01 wt %, preferably 10 wt % to 0.05 wt % and more preferably 5 wt % to 0.1 wt %, based on the weight of the monomer(s).

Preferably for the preparation of the (co)polymers only small amounts of organic solvents are used. If organic solvents are required, suitable solvents or mixtures of solvents are typically pure alkanes such as hexane, heptane or cycloalkane, carbonyl compounds such as methyl ethyl ketone, hydro-carbones such as benzene, toluene or xylene, halogenated hydrocarbons such as chlorobenzene, esters such as ethyl acetate, propyl, butyl or hexyl acetate, ethers such as diethyl ether, dibutyl ether or ethylene glycol dimethyl ether, alcohols such as methanol, ethanol, ethylene glycol or monomethyl ether or mixtures thereof of them. The solvent to monomer weight ratio is in the range from about 0 to 5, preferably from about 0 to 2.

The type of polymerization used may be bulk, solution, emulsion, dispersion or suspension polymerization and it may be carried out both batchwise and continuously.

The polymers prepared according to this invention show a low polydispersity ($M_w/M_n$) which is usually lower than 2 and may be significantly lower.

The number average molecular weight of the polymer chains increases linearly with the monomer conversion, which allows a tailor-made polymer molecular weight to be obtained. Furthermore, the molecular weight of the polymers may be controlled by varying the amount of crude alkoxyamine compared to the amount of monomers. High molecular weight polymers may be formed.

A further advantage of the present invention is that after the removal of the non-polymerized monomers from the (co)polymers or after reaching a conversion rate of 100%, a second polymerization step may be initiated simply by adding to the polymer synthesized in the first step a portion of fresh vinyl monomer or monomer mixture that may be different from the vinyl monomer or monomer mixture used in the first polymerization step. The polymerization of the vinyl monomer or monomer mixture added in the second step is then initiated by the polymer chains synthesized in the first polymerization step and di-block copolymers may be for example produced if the polymer chains synthesized in the first polymerization step consists of linear chains with one single growing chain end. The molecular weight and polydispersity of each block may be controlled independently during the respective polymerization step. This process may be repeated several times and may then provide multiblock copolymers of controlled molecular weight and molecular weight distribution for each block.

The resulting polymers are usually colorless and they may be used in most cases without any further purification.

The following Examples illustrate the invention in more detail.

EXAMPLES

The molecular weight was determined by gel permeation chromatography (GPC), equipped with a Shodex RI 74 differential refractometer. A flow rate of 1 ml/min was used and samples were prepared in THF. Polystyrene standards were used for calibration.

Example 1

Synthesis of p1-Phenyl-1-(2',2',6',6'-tetramethyl-1'-piperidinyloxy)-2-hydroxyethane 1 Using Oxone® (Potassium Monopersulfate, DuPont Specialty Chemicals, USA) as the Oxidizing Agent

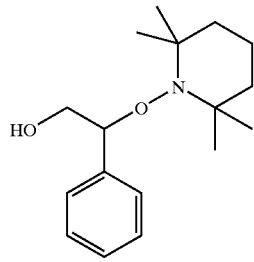

1

In a 500 ml four-necked round bottom flask equipped with a mechanical stirrer, a reflux, a thermometer, a funnel and a septum are added 40 g of water, 10 g $K_2CO_3$ (99%; $7.24 \cdot 10^{-2}$ mol), 5 g 2,2,6,6-tetramethylpiperidine (99%; $3.53 \cdot 10^{-2}$ mol) and 50 g toluene. Then, a solution of 21,702 g of Oxone® (Monopersulfate, DuPont Specialty Chemicals, USA) ($3.53 \cdot 10^{-2}$ mol) in 100 g water is slowly added to the 500 ml flask while stirring vigorously (with a slightly exothermic reaction) and the flask is placed in a water bath at room temperature. After the addition, the reaction medium is stirred at room temperature for 30 minutes, and the organic phase becomes progressively red due to the formation of 2,2,6,6-tetramethylpiperidine-1-oxide (TEMPO). Then, the reaction medium is heated at 40° C. for further 30 minutes.

The reaction medium is then cooled at room temperature, the stirring is terminated and the water phase is removed from the reaction flask. The red organic phase is then degassed by bubbling argon for 10 minutes. 11,124 g $FeSO_4 \cdot 7H_2O$ ($4 \cdot 10^{-2}$ mol) are then slowly added under an argon atmosphere and while stirring vigorously. Then, a degassed mixture of 100 ml methanol and 36.7 g of styrene ($3.53 \cdot 10^{-1}$ mol) are added rapidly to the reaction flask and the temperature is increased to 40° C. Finally, a solution of 13.71 g hydrogen peroxide (35%; 0.1412 mol) in 15 g methanol is added slowly (dropwise) for 28 minutes while keeping the temperature between 30 and 40° C. (with an exothermic reaction). When the addition is complete, the reaction mixture is allowed to react while stirring vigorously by room temperature for 2 h 30 mins.

The brown solution is then filtered and the residual styrene, hydrogen peroxide and methanol are then removed in vacuo at 50° C. To the viscous brown residue obtained is added 100 g of $CH_2Cl_2$ and 30 g of water, and then HCl is added until the pH is 3. The organic phase is then washed 2 times with an acidic solution (pH is 3) in order to remove the excess 2,2,6,6-tetramethylpiperidine. The organic phase is finally dried under $MgSO_4$, filtered and dried in vacuo at 50° C. 2.79 g of a viscous light yellow oil is obtained.

Example 2

Polymerization of Styrene Initiated by Non-purified 1-Phenyl-1-(2',2',6',6'-tetramethyl-1'-piperidinyloxy)-2-hydroxyethane 1 Synthesized in Example 1 Using Oxone® (Potassium Monopersulfate, DuPont Specialty Chemicals, USA) as the Oxidizing Agent To a three-necked round bottom flask equipped with a mechanical stirrer, a reflux condenser, a thermometer and a septum are added 0.3 g of non-purified 1 and 50 g of styrene (0.48 mol). The slightly yellow solution is then degassed by bubbling argon for 10 minutes, and is then heated at 125° C. Very rapidly, the solution becomes colorless.

After 7.5 h at 125° C., the polymerization medium is highly viscous and the polymerization is complete. After cooling, the polymer is dissolved with chloroform, transferred to an aluminum bag, dried overnight in air and then for 24 h at 70° C. in vacuo. The yield is calculated by gravimetric analysis.

Yield=80.6%; $M_n$=23250; $M_w$=33110; $M_w/M_n$=1.42.

Example 3

Random Copolymerization of Styrene and Acrylonitrile Initiated by Non-purified 1-Phenyl-1-(2',2',6',6'-tetramethyl-1'-piperidinyloxy)-2-hydroxyethane 1 Synthesized in Example 1 Using Oxone® (Potassium Monopersulfate, DuPont Specialty Chemicals, USA) as the Oxidizing Agent, and Subsequent Block Copolymerization with a Mixture of Methylmethacrylate, Styrene and Acrylonitrile Synthesis of Poly(styrene-co-acrylonitrile) (PSAN)

To a 250 ml three-necked round bottom flask equipped with a mechanical stirrer, a reflux condenser, a thermometer and a septum are added 0.3 g of non-purified 1 (synthesized in example 1), 75 g of styrene (0.72 mol) and 25 g of acrylonitrile (0.471 mol). The slightly yellow solution is then degassed by bubbling argon for 10 minutes, and is then heated at reflux for 9 h.

After 9 h under reflux, the polymerization medium is viscous. After cooling, the polymer is dissolved in chloroform, transferred to an aluminum bag, dried overnight in air and then heated for 24 h at 70° C. in vacuo. The yield is calculated by gravimetric analysis.

Yield=45.3%; $M_n$=53100; $M_w$=102960; $M_w/M_n$=1.93.

Synthesis of Poly(styrene-co-acrylonitrile)-b-poly(methylmethacrylate-co-styrene-co-acrylonitrile) Block Copolymer To a 500 ml four-necked round bottom flask equipped with a mechanical stirrer, a reflux condenser, a thermometer and a septum are added 20 g of PSAN synthesized in the first step, 75 g of styrene (0.72 mol), 25 g of acrylonitrile (0.471 mol) and 100 g of methylmethacrylate (1 mol). The colorless solution is then degassed by bubbling argon for 10 minutes, and is then heated under reflux for 10 h.

After 10 h under reflux, the polymerization medium is highly viscous and the polymerization is stopped. After cooling, the polymer is dissolved in chloroform, transferred to an aluminum bag, dried overnight in air and then heated for 24 h at 70° C. in vacuo. The yield is calculated by gravimetric analysis.

Yield=30%; $M_n$=86570; $M_w$=190430; $M_w/M_n$=2.19.

Chain extension of the starting PSAN is observed which confirms the controlled nature of the SAN (styrene and acrylonitrile) polymerization initiated by the non-purified alkoxyamine 1.

Example 4

Synthesis of 1-Phenyl-1-(2',2',6',6'-tetramethyl-1'-piperidinyloxy)-2-hydroxyethane 1 using Oxone® (Potassium Monopersulfate, DuPont Specialty Chemicals, USA) as the Oxidizing Agent: Scale-up To a 6 l four-necked round bottom flask equipped with a mechanical stirrer, a reflux condenser a thermometer, a funnel and a septum are added 634 g of water, 158.42 g $K_2CO_3$ (99%; 1,146 mol), 79.21 g 2,2,6,6-tetramethylpiperidine (99%; 5,607·10$^{-1}$ mol) and 792.1 g toluene. Then, a solution of 343.8 g of Oxone® (Monopersulfate, DuPont Specialty Chemicals, USA) (5.59·10$^{-1}$ mol) in 1584 g water is slowly added (over a period of 1 h 40 mins.) to the 6 l flask while stirring vigorously (slightly exothermic reaction) and the flask is placed in a water bath at room temperature. After the addition is complete, the reaction medium is stirred at room temperature for 30 minutes, and the organic phase becomes progressively red due to the formation of 2,2,6,6-tetramethylpiperidine-1-oxide (TEMPO). Then, the reaction medium is heated at 40° C. for a further 30 minutes.

The reaction medium is then cooled at room temperature, the stirring is terminated and the water phase is removed from the reaction flask. The red organic phase is then degassed by bubbling argon for 10 minutes. 176.23 g $FeSO_4 \cdot 7H_2O$ (6.34·10$^{-1}$ mol) are then slowly added in an argon atmosphere, while stirring vigorously. Then, a degassed mixture of 1584.2 g of methanol and 581.4 g of styrene (5,582 mol) is added rapidly to the reaction flask and the temperature is increased to 30° C. Finally, a solution of 217.19 g hydrogen peroxide (Merck, 35%; 2,235 mol) in 237,63 g methanol is slowly added (dropwise) for 5 h 40 minutes while keeping the temperature at between 30 and 40° C. When the addition is complete, the reaction mixture is allowed to react while stirring vigorously at room temperature for 15 h.

The brown solution is then filtered and the residual styrene, hydrogen peroxide and methanol are then removed in vacuo at 50° C. To the viscous brown residue obtained is added 1500 g of $CH_2Cl_2$ and 475 g of water, and then HCl is added until the pH is 3. The organic phase is then washed twice with an acidic solution (pH=3) in order to remove the excess 2,2,6,6-tetramethylpiperidine. The organic phase is finally dried under $MgSO_4$, filtered and dried in vacuo at 50° C. 121 g of a viscous light yellow oil is obtained.

In order to remove polystyrene formed during the reaction (optional step), the product is dissolved in chloroform and then precipitated in methanol. After filtration, the methanol phase is dried in vacuo and this operation is repeated once to obtain 71.35 g of a slightly yellow oil. This oil contains 1 and very low molecular weight polystyrene. The alkoxyamine 1 may be purified by flash chromatography or by high vacuum distillation, if necessary. For the controlled radical polymerization of vinyl monomers using alkoxyamine 1, it is not necessary to purify this alkoxyamine further. The slightly yellow oil may be directly used for polymerization.

Example 5

Random Copolymerization of Styrene and Acrylonitrile Initiated by the Non-purified 1-Phenyl-1-(2',2',6',6'-tetramethyl-1'-piperidinyloxy)-2-hydroxyethane 1 Synthesized in Example 4 Using Oxone® (Potassium Monopersulfate, DuPont Specialty Chemicals, USA) as the Oxidizing Agent To a 250 ml three-necked round bottom flask equipped with a mechanical stirrer, a reflux condenser, a thermometer and a septum are added 0.3 g of non-purified 1 (obtained in Example 4), 75 g of styrene (0.72 mol) and 25 g of acrylonitrile (0.471 mol). The slightly yellow solution is then degassed by bubbling through argon for 10 minutes and is then heated under reflux for 12 h. Samples are taken after 4.5 h, 8.25 h and 12 h and dried in vacuo at 70° C. and the conversion is finally calculated gravimetrically.

After 12 h under reflux, the polymerization medium is highly viscous and the polymerization is complete. After cooling, the polymer is dissolved in chloroform, transferred to an aluminum bag, dried overnight in air and heated for 24 h at 70° C. in vacuo.

| Sample | Time (h) | Conversion (%) | $M_n$ | $M_w$ | $M_w/M_n$ |
|---|---|---|---|---|---|
| 1 | 4.5 | 26.1 | 59200 | 105800 | 1.78 |
| 2 | 8.25 | 45.7 | 72350 | 122800 | 1.69 |
| 3 | 12 | 57.4 | 91950 | 144700 | 1.57 |

The molecular weight increases with the monomer conversion, as required in a controlled process. The polydispersity is high in the early stages of the polymerization but decreases as the monomer conversion increases. This observation is consistent with a controlled process.

Example 6

Synthesis of 1-Phenyl-1-(4'-Oxo-2',2',6',6'-tetramethyl-1'-piperidinyloxy)-2-hydroxyethane 2 Using Oxone® (Potassium Monopersulfate, DuPont Specialty Chemicals, USA) as the Oxidizing Agent

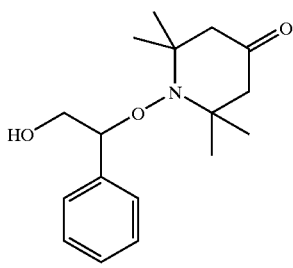
(2)

To a 2 l four-necked round bottom flask equipped with a mechanical stirrer, a reflux, a thermometer, a funnel and a septum are added 160 g of water, 35.40 g $K_2CO_3$ (99%; $2.56 \cdot 10^{-1}$ mol), 20 g 2,2,6,6-tetramethyl-4-piperidone (95%; $1.28 \cdot 10^{-1}$ mol) and 200 g toluene. Then, a solution of 173.62 g of Oxone ($2.82 \cdot 10^{-1}$ mol) in 700 g water is added slowly to the 2 l flask while stirring vigorously (with a slightly exothermic reaction) and the flask is placed in a water bath at room temperature. The starting brown-red solution becomes rapidly green when the Oxone® (potassium monopersulfate, DuPont Specialty Chemicals, USA) solution is added. After the addition is complete, the reaction medium is stirred at room temperature for 30 minutes and then at 40° C. for 1 h.

The reaction medium is then cooled at room temperature, the stirring is terminated and the water phase is removed from the reaction flask. The red organic phase is then degassed by bubbling argon for 10 minutes. 44.5 g $FeSO_4 \cdot 7H_2O$ ($1.6 \cdot 10^{-1}$ mol) are then slowly added under an argon atmosphere, while stirring vigorously. Then, a degassed mixture of 400 ml of methanol and 133.3 g of styrene (1.28 mol) are rapidly added to the reaction flask and the temperature is increased to 40° C. Finally, a solution of 49.78 g hydrogen peroxide (Merck, 35%; $5.12 \cdot 10^{-1}$ mol) in 60 g methanol is slowly added (dropwise) for 1 h while keeping the temperature between 30 and 40° C. When the addition is complete, the reaction is allowed to react while stirring vigorously at room temperature for 15 h.

The brown solution is then filtered and the residual styrene, hydrogen peroxide and methanol are then removed in vacuo at 50° C. To the viscous brown residue obtained is added 400 g of $CH_2Cl_2$ and 120 g of water, and then HCl is added until the pH is 3. The organic phase is then washed twice with an acidic solution (pH=3) in order to remove the excess 2,2,6,6-tetramethyl-4-piperidone. The organic phase is finally dried under $MgSO_4$, filtered and dried in vacuo at 50° C. 23.2 g of a viscous brown oil is obtained. This oil contains mainly the alkoxyamine 2, some residual 2,2,6,6-tetramethyl-4-piperidone and other unidentified molecules.

This brown oil may be used directly for polymerization without any intermediate purification.

Example 7

Random Copolymerization of Styrene and Acrylonitrile Initiated by the Non-purified 1-Phenyl-1-(4'-Oxo-2',2',6',6'-tetramethyl-1'-piperidinyloxy)-2-hydroxyethane 2 Synthesized in Example 6

To a 250 ml three-necked round bottom flask equipped with a mechanical stirrer, a reflux condenser, a thermometer and a septum are added 0.629 g of non-purified 2, 75 g of styrene (0.72 mol) and 25 g of acrylonitrile (0.471 mol). The slightly brown solution is then degassed by bubbling argon for 10 minutes and is then heated under reflux for 24 h.

After 24 h under reflux, the polymerization medium is solid and the polymerization is complete. After cooling, the polymer is dissolved in chloroform, transferred to an aluminum bag, dried overnight in air and then heated for 24 h at 70° C. in vacuo.

Yield=95.2%; $M_n$=55760; $M_w$=88650; $M_w/M_n$=1.59.

Example 8

Polymerization of Styrene Initiated by the Non-purified 1-Phenyl-1-(4'-Oxo-2',2',6',6'-tetramethyl-1'-piperidinyloxy)-2-hydroxyethane 2 Synthesized in Example 6

To a 250 ml three-necked round bottom flask equipped with a mechanical stirrer, a reflux condenser, a thermometer and a septum are added 0.629 g of non-purified 2, and 100 g of styrene (0.96 mol). The slightly brown solution is then degassed by bubbling argon for 10 minutes and is then heated at 125° C. for 12 h. Samples are taken from the reaction flask after 6 and 12 h. The polymer is dried in vacuo at 70° C. for 24 h and the conversion is calculated by gravimetric analysis.

After 12 h at 125° C., the polymerization medium is solid and the polymerization is stopped. After cooling, the polymer is dissolved in chloroform, transferred to an aluminum bag, dried overnight in air and heated for 24 h at 70° C. in vacuo.

| Sample | Time (h) | Conversion (%) | $M_n$ | $M_w$ | $M_w/M_n$ |
|---|---|---|---|---|---|
| 1 | 6 | 59.2 | 24830 | 41450 | 1.66 |
| 2 | 12 | 87.6 | 33620 | 54290 | 1.61 |

The molecular weight increases with the monomer conversion and the polydispersity remains low throughout the polymerization process as required in a controlled process.

Example 9

Synthesis of 1-Phenyl-1-(2',2',6',6'-tetramethyl-1'-piperidinyloxy)-2-hydroxyethane 1 Using Peracetic Acid as the Oxidizing Agent

To a 1 liter four-necked round bottom flask equipped with a mechanical stirrer, a reflux condenser, a thermometer, a funnel and a septum are added 80 g of water, 20 g $K_2CO_3$ (99%; 0.1448 mol), 10 g 2,2,6,6-tetramethylpiperidine (99%; 7,079·10$^{-2}$ mol) and 100 g toluene. Then, a solution of 15.34 g of peracetic acid (7.06·10$^{-2}$ mol) in 80 g water is added slowly to the 1 liter flask while stirring vigorously (with a slightly exothermic reaction) and the flask is placed in a water bath at room temperature. After the addition is complete, the reaction medium is stirred at room temperature overnight and the organic phase becomes red due to the formation of 2,2,6,6-tetramethylpiperidine-1-oxide (TEMPO).

The stirring is terminated and the water phase is removed from the reaction flask. The red organic phase is then degassed by bubbling argon for 10 minutes. 22.25 g $FeSO_4 \cdot 7H_2O$ (8·10$^{-2}$ mol) are then slowly added under an argon atmosphere, while stirring vigorously. Then, a degassed mixture of 200 ml methanol and 73.4 g of styrene (7.05·10$^{-1}$ mol) are added rapidly to the reaction flask and the temperature is increased to 40° C. Finally, a solution of 23.42 g hydrogen peroxide (Merck, 35%; 0.282 mol) in 30 g methanol is added slowly (dropwise) for 28 minutes while keeping the temperature at between 30 and 40° C. (with an exothermic reaction). When the addition is complete, the reaction mixture is allowed to react while stirring vigorously at 40° C. for 3 h.

The brown solution is then filtered and the residual styrene, hydrogen peroxide and methanol are then removed in vacuo at 50° C. To the viscous brown residue obtained are added 100 g of $CH_2Cl_2$ and 30 g of water and then HCl is added until the pH is 3. The organic phase is then washed 2 times with an acidic solution (pH=3) in order to remove the excess 2,2,6,6-tetramethylpiperidine. The organic phase is finally dried under $MgSO_4$, filtered and dried in vacuo at 50° C. 8.57 g of a viscous red oil is obtained. The red coloration is due to some unreacted 2,2,6,6-tetramethylpiperidine-1-oxide (TEMPO) formed by the oxidation of 2,2,6,6-tetramethylpiperidine by peracetic acid.

Example 10

Polymerization of Styrene Initiated by the Non-purified 1-Phenyl-1-(2',2',6',6'-tetramethyl-1'-piperidinyloxy)-2-hydroxyethane 1 Synthesized in Example 9 Using the Peracetic Acid as the Oxidizing Agent

To a three-necked round bottom flask equipped with a mechanical stirrer, a reflux condenser, a thermometer and a septum are added 0.6935 g of non-purified 1 (obtained in Example 9) and 100 g of styrene (0.96 mol). The slightly pink solution is then degassed by bubbling argon for 10 minutes and is then heated at 125° C.

Samples are taken from the reaction flask after 8 and 24 h, dried in vacuo at 70° C. and analysed by GPC. The conversion is calculated gravimetrically.

| Sample | Time (h) | Conversion (%) | $M_n$ | $M_w$ | $M_w/M_n$ |
|---|---|---|---|---|---|
| 1 | 8 | 25.1 | 9100 | 11570 | 1.27 |
| 2 | 24 | 79.7 | 23090 | 31610 | 1.36 |

The molecular weight increases linearly with the monomer conversion and the polydispersity is narrow as required in a controlled process. Compared to Example 2, the same molecular weights are obtained after about 80% monomer conversion, but the polymerization of styrene in Example 10 is slower.

Example 11

Random Copolymerization of Styrene and Acrylonitrile Initiated by the Non-purified 1-Phenyl-1-(2',2',6',6'-tetramethyl-1'-piperidinyloxy)-2-hydroxyethane 1 Synthesized in Example 9 Using Peracetic Acid as the Oxidizing Agent

To a 250 ml three-necked round bottom flask equipped with a mechanical stirrer, a reflux condenser, a thermometer and a septum are added 0.3 g of non-nurified 1 (obtained in Example 9), 75 g of styrene (0.72 mol) and 25 g of acrylonitrile (0.471 mol). The solution is then degassed by bubbling argon for 10 minutes and is then heated at reflux for 12 h. Samples are taken out after 8 h and 24 h, dried under vacuum at 70° C. and the conversion is finally calculated gravimetrically.

After 24 h under reflux, the polymerization medium is highly viscous and the polymerization is stopped. After cooling, the polymer is dissolved with chloroform, transferred to an aluminum bag, dried overnight in air and then for 24 h by 70° C. in vacuo.

| Sample | Time (h) | Conversion (%) | $M_n$ | $M_w$ | $M_w/M_n$ |
|---|---|---|---|---|---|
| 1 | 8 | 18.1 | 24470 | 37530 | 1.53 |
| 2 | 24 | 60.1 | 46290 | 63740 | 1.37 |

The molecular weight increases with the monomer conversion and the polydispersity is narrow as required in a controlled process.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A one-pot process for the preparation of functional alkoxyamines of the general formula (I),

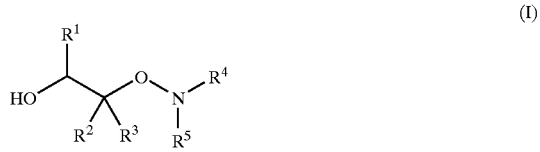

(I)

comprising
  (1) reacting in a water-containing medium, an oxidizing agent (A) with a sterically hindered secondary amine of the general formula (II), to produce an aqueous phase and a nitroxyl radical

 (II)

wherein
R⁴ and R⁵ are independently selected from the group consisting of $C_1$–$C_{18}$alkyl, $C_2$–$C_{18}$alkenyl, $C_2$–$C_{18}$alkynyl, $C_3$–$C_{12}$cycloalkyl, $C_3$–$C_{12}$-heterocycloalkyl, and $C_6$–$C_{24}$aryl, all of which are optionally substituted by a member selected from the group consisting of $NO_2$, halogen, amino, hydroxy, cyano, carboxy, ketone, $C_1$–$C_4$alkoxy, $C_1$–$C_4$alkylthio, and $C_1$–$C_4$alkylamino; or
R⁴ and R⁵ form, together with the nitrogen atom linking them, a $C_3$–$C_{12}$cycloalkyl radical, a ($C_4$–$C_{12}$alkanol)yl radical or a $C_2$–$C_{13}$heterocycloalkyl radical containing oxygen, sulfur or nitrogen atoms; or
R⁴ and R⁵ together form a residue of a polycyclic ring system or a polycyclic heterocycloaliphatic ring system containing oxygen, sulfur or nitrogen atoms;
wherein the carbon atom of R⁴ and R⁵ directly adjacent to the alkoxyamine nitrogen atom is in each case substituted by 3 further organic substituents and (2) removing of the aqueous phase and
(3) adding to the nitroxyl radical one or more vinyl monomer(s) of the general formula (III),

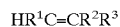 (III)

wherein
R¹, R², R³ are independently selected from the group consisting of hydrogen, $C_1$–$C_{20}$alkyl, $C_1$–$C_{20}$cycloalkyl $C_6$–$C_{24}$aryl, halogen, cyano, $C_1$–$C_{20}$alkylester $C_1$–$C_{20}$cycloalkylester, $C_1$–$C_{20}$alkylamide, $C_1$–$C_{20}$cycloalkylamide $C_6$–$C_{24}$-arylester or $C_6$–$C_{24}$-arylamide, and
(B) a system which produces free radicals that includes
(B1) a reducing agent and
(B2) a compound reactive with (B1) to form radicals.

2. The process of claim 1 wherein at least one of the radicals R⁴ and R⁵ contains a functional group Y which is capable of further reacting or cross-linking with functional groups known from the coatings field.

3. A process for polymerizing monomers comprising (i) obtaining the functional alkoxyamine of claim 1 and (ii) adding to the functional alkoxyamine at least one polymerizable monomer to form a reaction mixture and (iii) heating the reaction mixture, said functional alkoxyamine being unpurified.

* * * * *